United States Patent [19]

Custard et al.

[11] 4,363,632

[45] Dec. 14, 1982

[54] STABILIZED SOLUTION PRODUCING A ROMANOWSKY EFFECT

[75] Inventors: Elizabeth Custard, Mishawaka, Ind.; John C. Liao, Fort Worth, Tex.; John L. Ponzo, Mishawaka, Ind.

[73] Assignee: Miles Laboratories, Inc., Elkhart, Ind.

[21] Appl. No.: 335,227

[22] Filed: Dec. 28, 1981

[51] Int. Cl.$^3$ .............................................. C09B 00/00
[52] U.S. Cl. .......................................... 8/506; 8/602; 8/638; 8/644
[58] Field of Search .................... 8/506, 602, 638, 644

[56] References Cited

U.S. PATENT DOCUMENTS 4,290,769  9/1981  Liao et al. ............................... 8/602

OTHER PUBLICATIONS

E. Surr and N. Anand in "The Chemistry of Synthetic Dyes," vol. VII, (Vekataraman: Editor), Academic Press, 1974, pp. 278–279 and 287–288.
Histochemical Journal, 10 (1978), 1–29, P. N. Marshall, Romanowsky-Type Stains in Haemotology.

*Primary Examiner*—A. Lionel Clingman
*Attorney, Agent, or Firm*—Jerome L. Jeffers

[57] ABSTRACT

Disclosed is a cell-staining solution which contains Azure B, Eosin Y, and a stabilizing amount of diethylamine hydrochloride in methanolic solution, which produces a Romanowsky-type staining effect.

10 Claims, No Drawings

STABILIZED SOLUTION PRODUCING A ROMANOWSKY EFFECT

BACKGROUND OF THE INVENTION

Stains comprising mixtures of Methylene Blue and related thiazine dyes with Eosin are used routinely for the coloration of blood and bone-marrow films. These Romanowsky-type stains demonstrate the morphological features which distinguish the various haemopietic cells and those which characterize blood diseases. The term Romanowsky-type stain is commonly applied to any stain comprising Methylene Blue, its products of oxidation and a halogenated Fluorescein dye, usually Eosin Y. Successful Ramanowsky-type stains produce the Romanowsky effect. This may be defined as the condition in which the typical coloration of certain cell components results from the conbined action of a cationic and anionic dye, and cannot be produced by either dye acting along. It consists of the purple coloration of leucocyte chromatin and neutrophil granules and the magenta or carmine coloration of the nuclei of parasitic Protozoa. This effect is described as the result of some interaction of Azure B (an oxidation product of Methylene Blue) and Eosin Y by P. N. Marshall in his review of Romanowsky-type Stains in Haemotology appearing in Histochemical Journal 10 (1978) Pp. 1–29. This article also describes the phenomena of ageing the dye to cause it to stain mast cell granules red and the theory that Methylene Blue ages in solution to give some new dye which produces the proper staining. The requirement that the dye be aged was circumvented by boiling a solution of Methylene Blue with potassium carbonate to provide what became known as polychrome Methylene Blue. Wright's stain, extensively used in the United States, is a Romanowsky stain solution in which the Methylene Blue is polychromed by one or more known techniques and the product then mixed with Eosin Y. Polychroming results in a complex mixture of dyes including Azures B, C and A as well as leaving some Methylene Blue starting material in the final mixture. Marshall reports two disadvantages inherent in the polychroming of Methylene Blue. One is that the procedure results not only in the production of dyes essential for Romanowsky-type staining, but also in certain extraneous ones. He also states that the stain is not suitable for reproducible production on a commercial scale because polychroming cannot be effectively controlled on such a scale. The Marshall article reports the recent development of a reproducible stain suitable for commercial exploration, which avoids the polychroming process being comprised of purified Azure B and commercial Eosin Y whose methanolic stock solutions are prepared separately and mixed just prior to staining. These dye solutions are prepared separately and mixed just prior to use because the admixture of solutions of Azure B and Eosin Y results in the rapid formation of a precipitate which quickly renders the stain unsuitable for the intended purpose. It also appears that, in the typical Romanowsky-type stain, the Methylene Blue slowly oxidizes to Azure B and that the combination of Azure B and Eosin Y accounts for the desirable staining properties. The oxidation process will also continue in a sequence which will form other azure products that are not essential for staining but reduce the Azure B concentration. The Azure B formed by the gradual oxidation will form a reaction product with Eosin Y which precipitates from solution, but this precipitation is not as catastrophic as when Azure B and Eosin Y are combined directly in solution because of the gradual oxidation of Methylene Blue to Azure B. It would be desirable to provide a stabilized solution of Azure B and Eosin Y which would exhibit a reasonable shelf-life in order to aviod the step of mixing the separate solutions just before their use. U.S. Pat. No. 4,290,769, issued Sept. 22, 1981, discloses the stabilization of a Romanowsky-type stain solution comprising Methylene Blue, polychromed Methylene Blue products (azures) and an eosin dye with an alkylamine hydrohalide. Diethylamine hydrochloride is described as being a useful stabilizer for this three-component polychromed stain system. Unexpectedly, we have discovered that diethylamine hydrochloride is a suitable stabilizer for the much more unstable two-component system of Azure B and Eosin Y in methanolic solution.

SUMMARY OF THE INVENTION

The present invention is a stabilized staining solution which consists essentially of Azure B and Eosin Y in methanolic solution together with a stabilizing amount of diethylamine hydrochloride.

DESCRIPTION OF THE INVENTION

Azure B and Eosin Y are very soluble in methanol individually. However, a mixture of Azure B and Eosin Y in methanol produces a heavy precipitate within a few hours at ambient temperature. Thus, while a fresh mixture of solutions of the two dyes provides satisfactory performance of blood smears, the useful shelf-life of the solution is severely limited.

In preparing the stain solution of the present invention, we prefer to combine the Eosin Y with the diethylamine hydrochloride before introducing Azure B to the methanol solution. This is the case because we believe the diethylamine hydrochloride interacts with the Eosin Y to form a chemical species which does not react with Azure B to form a precipitate. Upon addition of Azure B to the solution, no rapid precipitation is observed, and the solution provides an excellent Romanowsky staining effect.

In a typical stain solution, the amount of Eosin Y dissolved in methanol will range from 0.062 to 0.104 percent on a weight/volume basis (W/V) and preferably from 0.078 to 0.088 percent. The concentration of Azure B is typically from 0.032 to 0.080 percent (W/V) with a concentration of from 0.043 to 0.047 percent being preferred. For best staining results, the ratio of Eosin Y to Azure B should be from 2.05:1 to 1.66:1 on a dry weight basis. The amount of diethylamine hydrochloride employed is a stabilizing amount; i.e. that amount which will significantly reduce their precipitation when the dyes are placed in methanol solution. We prefer to employ an amount of diethylamine hydrochloride equal to from 0.24 to 0.64 percent of the stain solution on a weight/volume basis.

The method of practicing the invention is further illustrated by the following example:

EXAMPLE I

Diethylamine hydrochloride, 11.52 g (0.48% W/V) and Eosin Y, 2.11 g (0.0879% W/V), were mixed thoroughly with 2.4 liters of methanol for 20 minutes. After holding overnight (16 hours) at ambient temperature, Azure B, 1.768 g (0.074% W/V), was introduced. The solution was mixed thoroughly for 20 minutes and then held at ambient temperature for several hours before filtration to remove any solids. The component stain solution was found to produce a Romanowsky-type effect as indicated by the performance data in Table I.

TABLE 1

THE DIFFERENTIAL STAINING PERFORMANCE OF COMPONENT STAIN SOLUTIONS ON BLOOD SMEARS BEFORE AND AFTER STRESS AT 50° C.

| Stress Time | Neutrophils | | Eosinophils | | Lymphocytes | | Monocytes | | Red Blood Cells | Platelets |
|---|---|---|---|---|---|---|---|---|---|---|
| | N* | C* | N | C | N | C | N | C | | |
| 0 Day, Original | 4.9 ± 0.2** | 4.7 ± 0.4 | 4.5 ± 0.4 | 4.7 ± 0.3 | 4.9 ± 0.2 | 4.9 ± 0.2 | 4.6 ± 0.2 | 4.7 ± 0.2 | 4.4 ± 0.4 | 4.8 ± 0.3 |
| 28 Days | 4.5 ± 0.0 | 4.3 ± 0.3 | 4.2 ± 0.3 | 4.8 ± 0.3 | 4.7 ± 0.2 | 4.6 ± 0.2 | 4.3 ± 0.3 | 4.3 ± 0.3 | 4.3 ± 0.3 | 4.3 ± 0.3 |

*N = Nucleus; C = Cytoplasm
**Average ± s (n = 6); 5, excellent; 4, good; 3, satisfactory; <3, not satisfactory.

No precipitate was observed for more than two months at 23° C., 40° C. and 50° C. stability stress. However, this stain solution did form a small amount of precipitate after storage at 5° C. for 20 days, so prolonged cold storage should be avoided.

The combination of Eosin Y and Azure B in methanol resulted in catastrophic precipitation; i.e. the precipitate began forming immediately and continued to form to the extent that within 2 to 3 hours the solution contained insufficient stain for proper blood staining effects which prohibited further work with the unstabilized solution.

The stain disclosed herein is not classified as a Romanowsky-type stain because Methylene Blue is present in all such stains. Although Methylene Blue is not an essential component for staining, it is very similar in structure to Azure B and is considered to be a contributing factor in formation of the 1:2 ion pair of Eosin Y:blue component. A conventional polychromed Romanowsky-type stain is relatively more stable than the stain solutions comprising only Eosin Y and Azure B under cold stress. Conventional polychromed stain solutions without the stabilizer, diethylamine hydrochloride, produced precipitate at 5° C. after about 50 days of stress. It appears that Methylene Blue may behave as a secondary system stabilizer in a conventional polychromed stain to retard but no eliminate precipitate formation. Since the typical Romanowsky-type stain comprising three dyes; i.e. an azure, Methylene Blue and an eosin, is somewhat more stable than that containing only Azure B and Eosin Y it, therefore, must be stabilized only for long-term storage as described in aforemetioned U.S. Pat. No. 4,290,769. Since Methylene Blue itself serves as a stabilizer which will retard but not eliminate precipitate formation, it was unexpected that diethylamine hydrochloride would stabilize the two dye, Azure B/Eosin Y, system. The three dye system is still preferred when long-term stability is required since during cold shock tests it did not produce substantial precipitate for 50 days at 5° C. However, there are advantages to use of the stabilized two dye system when shorter term stability is satisfactory since the problems associated with the use of polychromed Methylene Blue are eliminated. For example, conventional stain formulations utlizing polychromed dye powder are found to have significant batch-to-batch performance variations because of non-reproducible dye composition, i.e. Azure B and numerous other oxidation products, and metal salt contamination which causes de-staining. The avoidance of polychromed dye and use of individual pure dye components eliminates these problems.

What is claimed is:

1. In combination with a blood staining solution consisting essentially of Azure B and Eosin Y in methanolic solution, the improvement which comprises the presence of diethylamine hydrochloride in such solution.

2. The improved staining solution of claim 1 wherein the amount of Eosin Y is from 0.062 to 0.104 percent, the amount of Azure B is from 0.032 to 0.080 percent and the amount of diethylamine hydrochloride is from 0.24 to 0.64 percent of the stain solution all on a weight/volume basis in an amount which will significantly reduce precipitation of the Azure B and Eosin Y from such solution.

3. The improved staining solution of claim 2 wherein the amount of Eosin Y is from 0.078 to 0.088 percent and the amount of Azure B is from 0.043 to 0.047 percent.

4. The improved staining solution of claim 2 wherein the ratio of Eosin Y to Azure B is from 2.05:1 to 1.66:1 on a dry weight basis.

5. The improved staining solution of claim 3 wherein the ratio of Eosin Y to Azure B is from 2.05:1 to 1.66:1 on a dry weight basis.

6. A method for the preparation of a blood staining solution which comprises combining Eosin Y and diethylamine hydrochloride in methanol to form their methanolic solution and then adding Azure B to the solution to form a stabilized staining solution consisting essentially of the reaction product of Eosin Y and diethylamine hydrochloride and Azure B said diethylamine hydrochloride being present in an amount sufficient to reduce significantly the precipitation of Azure B and Eosin Y.

7. The method of claim 6 wherein the amount of Eosin Y is from 0.062 to 0.104 percent, the amount of Azure B is from 0.032 to 0.080 percent and the amount of diethylamine hydrochloride is from 0.24 to 0.64 percent of the staining solution all on a weight/volume basis.

8. The method of claim 7 wherein the amount of Eosin Y is from 0.078 to 0.088 percent and the amount of Azure B is from 0.043 to 0.047 percent.

9. The method of claim 7 wherein the ratio of Eosin Y to Azure B is from 2.05:1 to 1.66:1 on a dry weight basis.

10. The method of claim 8 wherein the ratio of Eosin Y to Azure B is from 2.05:1 to 1.66:1 on a dry weight basis.

* * * * *